United States Patent [19]

Valenty et al.

[11] Patent Number: 4,639,325

[45] Date of Patent: Jan. 27, 1987

[54] DETERGENT BUILDER

[75] Inventors: Vivian B. Valenty, Schenectady, N.Y.; William H. Hill, Cedar City, Utah; Prasad S. Ravi, Decatur, Ill.

[73] Assignee: A. E. Staley Manufacturing Company, Del.

[21] Appl. No.: 829,678

[22] Filed: Feb. 14, 1986

Related U.S. Application Data

[63] Continuation-in-part of Ser. No. 664,451, Oct. 24, 1984, abandoned, which is a continuation-in-part of Ser. No. 575,421, Jan. 31, 1984, Pat. No. 4,524,009.

[51] Int. Cl.$^4$ .............................................. C11D 1/08
[52] U.S. Cl. ..................... 252/89.1; 252/82; 252/174.18; 252/174.19; 252/180; 252/DIG. 11; 562/583
[58] Field of Search ................... 562/583; 252/180, 82, 252/89.1, DIG. 11, 174.24, 174.19, 174.18

[56] References Cited

U.S. PATENT DOCUMENTS

| | | | |
|---|---|---|---|
| 3,128,287 | 4/1964 | Berg | 260/346.8 |
| 3,692,685 | 9/1972 | Lamberti | 252/89 |
| 3,954,858 | 5/1976 | Lamberti | 260/535 P |
| 4,002,676 | 1/1977 | Borggrefe | 260/535 P |
| 4,017,541 | 4/1977 | Stubbs | 260/535 P |
| 4,019,999 | 4/1977 | Ohren | 252/140 |
| 4,021,376 | 5/1977 | Lamberti | 252/542 |
| 4,025,450 | 5/1977 | Lamberti | 252/89 R |
| 4,219,672 | 8/1980 | Borggrefe | 562/583 |
| 4,524,009 | 6/1985 | Valenty | 252/89.1 |

OTHER PUBLICATIONS

Organic Builders: A Review of Worldwide Efforts to Find Organic Replacements for Detergent Phosphates—M. M. Crutchfield, JAOCS, vol. 55, pp. 58–65 (1/78).
Organic Builder Salts as Replacements for Sodium Tripolyphosphate (I) and (II), E. A. Matzner et al., Tenside Detergents—10, pp. 119–125 and 239–245 (1973).
Nitrogen-and Phosphorous-Free Strong Sequestering Builders—H. C. Kamper et al., Tenside Detergents—12, pp. 47–52 (1975).

*Primary Examiner*—Paul Lieberman
*Assistant Examiner*—Hoa Van Le
*Attorney, Agent, or Firm*—Philip L. Bateman; James B. Guffey; Michael F. Campbell

[57] ABSTRACT

Products which are useful as detergent builders and which do not contain nitrogen or phosphorous atoms are described. Such detergent builders comprise one or more compounds of the Formula I-V below:

$$[MOOCCH_2(MOOC)CHOCH_2]_2CHOCH(COOM)CH_2COOM \quad (I)$$

$$HOCH_2CH(OH)CH_2OCH(COOM)CH_2COOM; \quad (II)$$

$$HOCH_2CH[OCH(COOM)CH_2COOM]CH_2OCH(COOM)CH_2COOM; \quad (III)$$

$$MOOCCH_2(MOOC)CHOCH_2CH(OH)CH_2OCH(COOM)CH_2COOM; \quad (IV)$$

or $$HOCH_2CH[OCH(COOM)CH_2COOM]CH_2OH \quad (V)$$

wherein M is a salt-forming cation or hydrogen or mixtures thereof. Such compounds and/or mixtures thereof are produced by reacting glycerin with maleic acid (or a source thereof) in the presence of an alkaline earth metal hydroxide.

37 Claims, 1 Drawing Figure

THE SEQUESTRATION OF Ca$^{++}$ BY GTS AND KNOWN BUILDERS VIA THE Ca$^{++}$ ELECTRODE METHODE

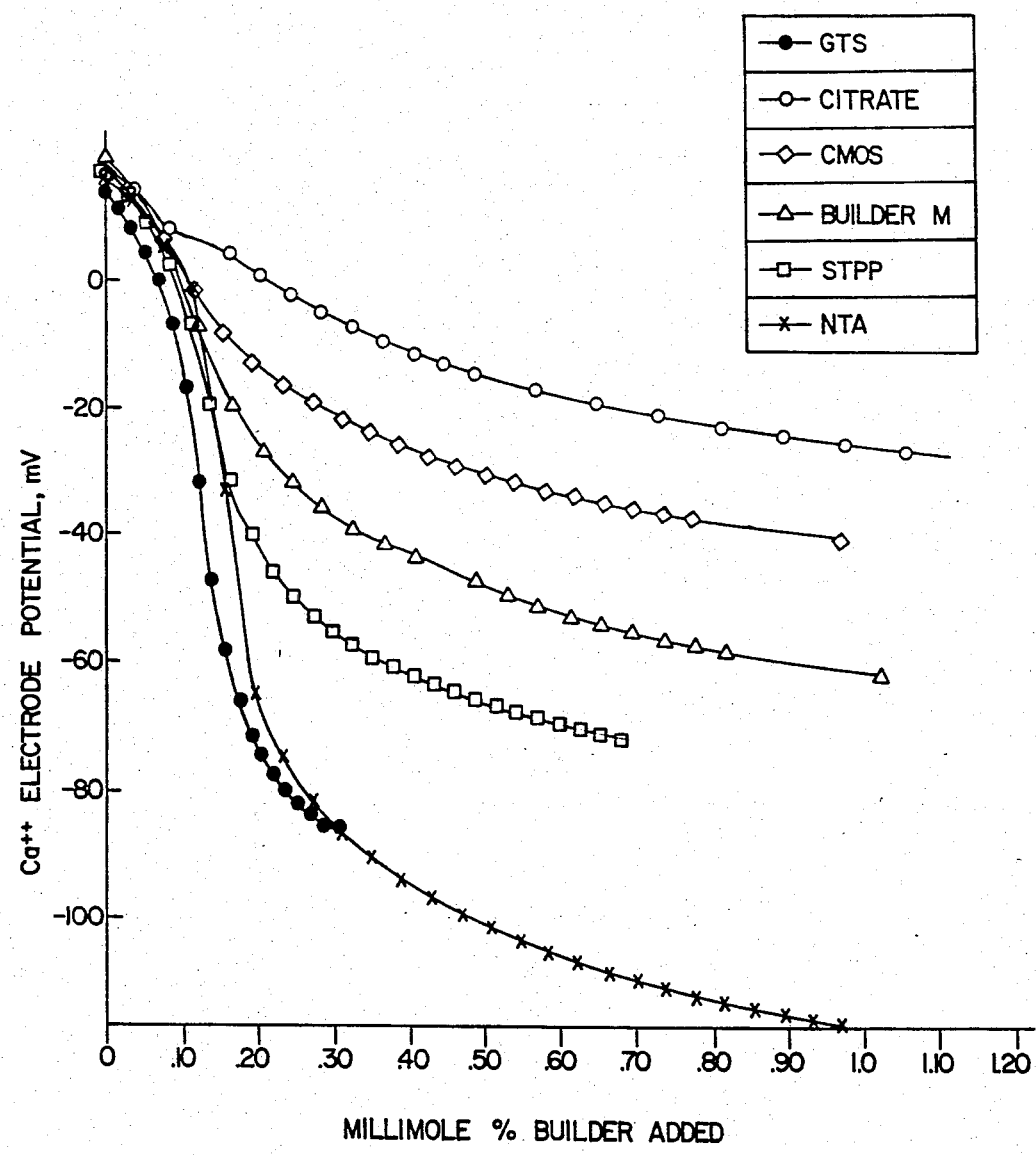

DETERGENT BUILDER

CROSS-REFERENCE TO RELATED APPLICATION

This application is a continuation-in-part of Ser. No. 664,451 (filed Oct. 24, 1984) now abandoned which was in turn a continuation-in-part of Ser. No. 575,421 (filed Jan. 31, 1984) which issued on June 18, 1985 as U.S. Pat. No. 4,524,009 and which is incorporated by reference.

BACKGROUND OF THE INVENTION

1. Field Of The Invention

This invention describes detergent builder materials which are suitable as partial or total replacements for phosphates or nitrogen-containing builders.

2. Description Of The Art Practices

Detergent builders are used to enhance the activity of the detergent or surfactant material used for cleaning. A detergent product typically contains a surface-active material (surfactant) which is used to lift dirt from the fabrics and to penetrate into the fabrics to remove embedded soil. Typically, these surface-active agents are the sodium salts of anionic materials. As the bulk of heavy-duty detergents are of the anionic nature, there exists an interference in the cleaning mechanism when calcium or magnesium ions (which are present as water hardness or body soil) react with the anion. In the case of body soil, the surfactant will become fixed onto the fabric due to the formation of the insoluble calcium or magnesium salt. The calcium or magnesium cations within the water cause the surfactant to be inactivatedd due to the formation of insoluble salts.

Heavy-duty liquid detergent products have been difficult to formulate utilizing currently available detergent builders. This is most evident as the common detergent builders employed tend to be phosphate salts which precipitate out of a liquid composition when utilized at an effective amount for cleaning. Although heavy-duty liquid detergent products are often formulated with a substantial amount of a nonionic surfactant such as ethoxylated alcohol which is not metal ion sensitive, the ability of calcium and magnesium ions to fix on the soil leads to the desirable inclusion of a detergent builder.

As mentioned previously, phosphate salts such as sodium tripolyphosphate or sodium pyrophosphate have been extensively used. Several states have outlawed the use of phosphorous-containing compounds in detergent products due to the eutrification caused by the presence of the phosphates. Replacements for phosphates as builders in detergent products have included organic nitrogen-containing compounds, carbonates and aluminosilicates. Each of these materials has its own particular negatives associated therewith. For instance, concern has been expressed over the widespread usage of organic nitrogen-containing compounds due to potential carcinogenic effects and their propensity to chelate desirable heavy metal ions in the environment. Carbonates have been widely employed but are generally ineffective as detergent builders as they result in the build-up of scale due to insoluble calcium carbonate formation. Aluminosilicates are insoluble materials commonly used in water softeners. The aluminosilicates are disadvantageous in that, as an insoluble material, they may be retained upon clothing or fabric and may cause excessive wear of washing machine components. The aluminosilicates are also not useful in liquid products due to their insolubility.

It is, therefore, desirable to formulate detergent products containing builders which do not contain nitrogen or phosphorous and which are water-soluble and are biodegradable. It has been reported in an article entitled "Nitrogen-and Phosphorous-Free Strong Sequestering Building", Kemper et al, *Tenside Detergents,* 12 page 47–51 (1975) that the reaction product of ethylene glycol and dimethyl diazomalonate results in such a compound. While this material avoids the presence of phosphorous or nitrogen in the final product, its preparation requires the handling of hazardous diazo compounds and requires exaggerated temperature and the use of copper as a catalyst to form the desired compound, thereby imparting relatively high costs to the final product. The efficacy of this compound as reported by the authors is rated at about 97% of sodium tripolyphosphate. Other compounds disclosed in the Kemper reference show Builder M (2-oxa-1,1,3-propanetricarboxylic acid) at 93% of sodium tripolyphosphate. A further proposed material 2-oxa-1,3,4-butanetricarboxylic acid (CMOS) is rated at only 90% of sodium tripolyphosphate.

It is further recommended by the present authors that the reader review U.S. Pat. No. 3,692,685, issued to Lamberti et al on Sept. 19, 1972, as well as U.S. Pat. No. 3,128,287, issued to Berg on Apr. 7, 1964. Further disclosures of carboxylic acid materials are found in U.S. Pat. No. 4,021,376 issued to Lamberti et al on May 3, 1977.

German Pat. No. 2,147,780, published on Mar. 29, 1973, to Kandler et al and German Pat. No. 2,408,591, published on Sept. 4, 1975, to Borggrefe et al, also concern the general subject matter of the present invention. The article of Crutchfield entitled "Organic Builders: A Review of Worldwide Efforts to Find Organic Replacements for Detergent Phosphates" published in the *JAOCS* 55, pages 58–65 (1978), and the Matzner et al article entitled "Organic Builder Salts as Replacements for Sodium Tripolyphosphate (I)" in *Tenside Detergents,* 10, pages 119–125 and 239–245 (1973) also provide useful information concerning the general scope of the present invention. Further information on detergent products is found in Stubbs et al U.S. Pat. No. 4,017,541 issued Apr. 12, 1977 and Borggrefe's U.S. Pat. Nos. 4,002,676 and 4,219,672 issued Jan. 11, 1977 and Aug. 26, 1980 respectively.

To the extent that each of the foregoing references are pertinent to this disclosure, they are herein incorporated by reference.

The present invention deals with the formation of a detergent builder from readily available materials which do not contain phosphorous or nitrogen. The new builder is biodegradable, is readily soluble in water and has superior detergent builder capabilities over known related compounds.

Throughout the specification and claims, percentages and ratios are by weight, pressures are in atmospheres and temperatures are in degrees Celsius unless otherwise indicated.

SUMMARY OF THE INVENTION

This invention describes compounds of the formula:

[MOOCCH$_2$(MOOC)CHOCH$_2$]$_2$CHOCH(COOM)CH$_2$COOM    (I)

HOCH$_2$CH(OH)CH$_2$OCH(COOM)CH$_2$COOM  (II)

HOCH$_2$CH[OCH(COOM)CH$_2$COOM]CH$_2$OCH(COOM)CH$_2$COOM  (III)

MOOCCH$_2$(MOOC)CHOCH$_2$CH(OH)CH$_2$OCH(COOM)CH$_2$COOM  (IV)

HOCH$_2$CH[OCH(COOM)CH$_2$COOM]CH$_2$OH  (V)

wherein M is a salt-forming cation or hydrogen or mixtures thereof.

Mixtures of the foregoing are included herein as well as the product obtained from the process of reacting glycerin and a source of maleic acid in the presence of an alkaline earth hydroxide.

The invention also describes a method of cleaning fabrics through the use of the foregoing compounds to control calcium, magnesium and iron ions during the cleaning process.

DESCRIPTION OF THE DRAWING

The drawing shows the molar concentrations of selected builders versus calcium ion electrode potentials. The proximity of the curve to the Y-axis shows the ability to sequester free calcium ion at low molar concentrations of the builder. Proximity of the curve to the X-axis shows the ability to control free calcium ion to low levels in the solution. The latter point is helpful in cleaning as the residual free calcium level is still capable of binding soil to fabrics.

GTS, which represents a reaction product of glycerin and maleic acid composed predominantly of the compound of the formula I, is superior to all the other builders tested in its ability to control free calcium ions at relatively low molar concentrations. GTS is also seen to be second only to NTA at higher molar concentrations in its ability to control calcium to low levels. The other builders in the test (all sodium salts) were nitrilotriacetate (NTA); tripolyphosphate (STPP); CMOS; citrate; and Builder M.

DETAILED DESCRIPTION OF THE INVENTION

The backbone of the claimed components of the present invention is glycerin. Glycerin is a trihydroxylic compound containing two primary hydroxyl groups and one centrally located secondary hydroxyl group. A primary compound of interest herein is the trisubstituted product I. The secondary materials obtained herein include the 1,2 (Compound III) and 1,3 (Compound IV) disubstituted materials; the 1 (being equivalent with the 3 position) substituted mono adduct (Compound II) and the 2 substituted mono adduct (Compound V). Glycerin is a readily available material and any source may be utilized to obtain the compounds described herein.

The second reactant material in the present invention is preferably maleic anhydride. Maleic acid may also be used, however, maleic anhydride is less expensive and readily available. If it is desired to conduct the reaction through maleic acid, the maleic anhydride may be simply converted through the addition of water to give the corresponding acid. As used herein, the term source of maleic acid is defined to mean a material which will generate maleic acid and which is useable to give the products of the present invention.

The ratio of maleic acid source to glycerin employed in the present process will typically range from about 1 to about 4 or more moles of maleic acid source per mole of glycerin. In those instances wherein it is desired that the reaction product be predominantly composed of the formula I compound, at least about 3 (preferably at least about 3.5 or 4) moles of maleic acid source will generally be employed per mole of glycerin.

In those instances wherein it is desired to have relatively higher levels of the compounds of the formulas II–V in the resulting reaction product, from about 1 to about 2.5 moles of maleic acid source will generally be employed per mole of glycerin.

Water is generally present in the reaction mixture hereof in an amount ranging from about 15 to about 70 weight percent on a total reaction mixture weight basis and is preferably employed in an amount ranging from about 20 to about 50 (more preferably from about 20 to about 40) weight percent on a total reaction mixture weight basis.

An alkaline earth catalyst, preferably calcium hydroxide, is utilized in the formation of the desired compounds. As the hydroxide is both a catalyst and a preferred method of keeping the pH within the desired range, it will be added as necessary to maintain the pH within the desired range. The pH of the reaction mixture is preferably greater than 10 and less than 14, with a desirable range being from about 10.5 to 12.5. The pH may be further adjusted with caustic. At the end of the reaction time, the alkaline earth ions (e.g. calcium or magnesium from the respective hydroxides) may be removed by precipitation with soluble salts such as sodium carbonate, sodium bicarbonate, sodium sulfate, etc. which form insoluble calcium salts. The resulting calcium-containing precipitate may then be filtered off leaving the sodium salt of the compounds of the Summary in the aqueous solution. Similarly, the potassium or lithium salts may be obtained as well as the ammonium and substituted ammonium salts. If desired the alkaline earth metal salt of compounds (I–V) may be recovered directly from the reaction mixture.

As used herein, the terms "alkaline earth hydroxide" and "alkali metal hydroxide" are to be understood as also encompassing alkaline earth oxides and alkali metal oxides, respectively. Such oxides can be used directly in the subject reaction process or can be converted in a preliminary step to the corresponding hydroxide by dissolution in water.

In an especially preferred embodiment, the reaction between the glycerin and the maleic acid source is conducted in the presence of both an alkaline earth hydroxide (preferably calcium hydroxide) and an alkali metal hydroxide (preferably sodium or potassium hydroxide). In such embodiment, it is generally preferred to add the alkali metal and alkaline earth metal hydroxide materials to the glycerin prior to adding the maleic acid source thereto. It is also generally preferred within such embodiment to add the alkali metal hydroxide material to the reaction mixture prior to adding the alkaline earth metal hydroxide catalyst thereto. Also within this particular embodiment, it is generally preferred to employ the indicated hydroxide materials in an alkaline earth hydroxide to alkali metal hydroxide mole ratio of from about 9:2 to about 1:18 (more preferably from about 3:2 to about 1:6 and most preferably from about 3:4 to about 1:3).

The alkaline earth hydroxide (or combination thereof with alkali metal hydroxide) is generally employed in an amount sufficient to provide a hydroxide equivalent weight at least equal to (and preferably at least about 10 percent in excess of) the carboxyl equivalent weight of the maleic acid source employed in the subject reaction.

In those instances wherein the alkaline earth hydroxide is used alone (i.e., without an alkali metal hydroxide component), it is generally preferred to add the maleic acid source to the glycerine-containing reaction mixture prior to adding said alkaline earth hydroxide catalyst thereto.

In conducting the aforementioned reaction process, maleic anhydride can suitably be employed as the maleic acid source and can be directly used as such (i.e., without preliminary hydrolysis) in the reaction or can, if desired, be subjected to hydrolysis (either complete or partial, as desired) with water to convert it to maleic acid form prior to use in said reaction process. In either event, the chosen form of the maleic acid source can be incorporated into the reaction mixture via a single addition thereof or can be gradually or incrementally added thereto in two or more (equal or unequal) portions during the course of the reaction process. In those instances where incremental maleic acid or anhydride addition is selected, it is generally preferred to also employ incremental addition of the alkaline earth hydroxide component (or alkaline earth plus alkali metal hydroxide components) in portions generally proportional to the relative size of those of the acid or anhydride additions and preferably just after or before, as desired, the individual acid or anhydride additions.

In one particularly preferred process, an initial mixture comprising glycerin, an alkali metal hydroxide, an alkaline earth hydroxide and water is initially prepared; non-hydrolyzed maleic anhydride is employed as the maleic acid source; substantially all of the maleic anhydride is added to the indicated initial mixture in a single controlled addition; and the reaction is conducted under reflux conditions. Since the reaction which occurs upon the addition of maleic anhydride is quite exothermic, care should be exercised to avoid overpowering the reflux condenser and causing undesirable viscosity buildup in the reaction mixture due to excessive loss of water.

The temperature during the formation of the compounds of the present invention is conveniently maintained in the reactor at greater than 50° C., typically from 50° C. to 125° C., preferably 60° C. to 120° C.

The crude product may be further purified by the following procedure: The reaction mixture is initially acidified to a pH of about 2 with an acid such as concentrated hydrochloric. The addition of the acid will result in the precipitation of fumaric acid by-product which is then filtered from the reaction mixture. The filtrate may be evaporated to dryness in a rotary evaporator and the resulting dried residue extracted with an excess of 2-butanol to separate the product from inorganic salts. This product is then filtered and the filtrate is evaporated to dryness. The product can then be converted to the alkali metal salt by neutralization with alkali metal hydroxide and used for its intended purpose. Alternatively, the product can, if desired, be further purified by extraction with acetone prior to neutralization with the alkali metal hydroxide. It should also be noted that the salts of the compounds of the present invention may also be used as a leached corrosion inhibitor such as by pumping the product into a well-hole and allowing it to slowly solubilize thereby protecting the piping in the well-hole from corrosion.

The reaction product as obtained from the hereinbefore described reaction process will typically comprise a mixture of compounds of the formulas I–V, inclusively. Such reaction product mixture is suitably, conveniently and preferably employed directly as a detergent builder ingredient without fractionation, isolation and/or purification of its individual formula I–V component species.

If desired, however, the individual compound species of the formulas I–V, respectively, can be isolated and separately recovered by generally known chromatographic fractionation techniques using commercially available cation exchange resins such as, for example, sulfonic acid ion exchange resins, etc.

The products of the present invention are conveniently used as detergent builders in formulations with surfactants which include alkyl ether sulfates, alkyl benzene sulfonates, alkyl sulfates, olefin sulfonates, paraffin sulfonates, alkoxylated alcohols (especially ethoxylated alcohols) and alkyl polyglycosides and mixtures thereof. Conveniently, the novel detergent builders of the present invention are utilized in a weight ratio of from about 4:1 to about 1:4, preferably 3:1 to 1:3 by weight to the surfactant. The detergent products which may be formulated according to the present invention are conveniently used at from about 0.05 to 1% by weight of the wash liquor, e.g. water.

Detergent products formulated according to the present invention may also include a co-builder such as carboxymethyloxysuccinate (2-oxa-1,3,4-butanetricarboxylic acid); Builder M (2-oxa-1,1,3-propane-tricarboxylic acid); zeolites including the type referred to in U.S. Pat. No. 4,019,999 issued Apr. 26, 1977 to Ohren et al. Similarly, citrates, carbonates and various phosphates including tripolyphosphate, pyrophosphates, and othophosphates may be utilized as co-builders. The phosphate materials and a material such as the salts of nitrilotriacetic acid which may be used are, for the foregoing reasons, undesirable due to their environmental consequences. Nonetheless, should specific uses be desired, such materials may be utilized. The builders (I), (II), (III), (IV), and (V) are conveniently used in a weight ratio of 8:1 to 1:8 with each other. Particularly effective are mixtures of (I) with (III) and/or (IV). Mixtures of (I) and (II) as well as (I) through (V) are also useful.

Other convenient materials which may be utilized in formulating detergent products include sodium sulfate which is typically used as a structurant in a detergent product and sodium silicate which is useful as a structurant in granular detergent products and as well to protect washing machine surfaces from corrosion. Silicates also function to control pH in the wash liquor. Anticaking agents for granular products, and hydrotropes and viscosity agents may be included for liquid products. Optical dyes and brighteners are also useful in combination with the builders of this invention.

The following are suggested exemplifications of the present invention:

EXAMPLE I

A mixture is prepared containing three moles of glycerin, 5.25 moles of calcium hydroxide, 11.55 moles caustic, and 42 moles of water. The reaction is initiated by adding 10.5 moles of maleic anhydride. The mixture is vigorously stirred and the temperature is maintained at about 90° C. during addition of the maleic anhydride. The pH is maintained between 11 and 12 and the reaction is allowed to continue at reflux for about 2.5 hours.

The reaction is now essentially complete and the reaction mixture is allowed to cool. At this time about 5.51 moles of sodium carbonate in 125 moles water are added with vigorous stirring. The addition of sodium carbonate causes calcium present in the reaction mixture to precipitate. The calcium carbonate is then filtered off after the reaction has been cooled to room temperature. The filtrate is found to contain Compound (I) of the Summary of the Invention by fractionation of the reaction product using high performance liquid chromatography (sulfonic acid ion exchange resin packing); preparation of the methyl ester of the major fraction (via reaction with methanol in the presence of an acid catalyst); purification of the methyl ester product using silica gel chromatography; and structural characterization by nuclear magnetic resonance (NMR), mass spectrometry and infrared (IR) spectroscopy techniques. Compound (I) of the present invention is determined to effectively sequester calcium ions from solution.

EXAMPLE II

A mixture of 0.45 parts of linear dodecyl benzene sulfonate and 0.25 parts of the builder of Example I are added to 1000 parts of water containing calcium and magnesium for a total hardness level of 200 ppm as calcium carbonate in a 3:2 calcium to magnesium ratio. The mixture is adjusted to pH 9.0 and transferred to a tergotometer bucket which is preheated to 40.5° C. After agitation for 30 seconds, 6 soiled cloth (dacron/cotton blend) swatches with known reflectance values are added to each bucket. Agitation is continued at 125 rpm for 15 minutes. The cloth swatches are rinsed in water at 37° C. for 2 minutes and then dried in a clothes dryer for 15 minutes. The dried swatches are ironed before determination of the change in reflectance is made. The results show the builder of Example I to be effective.

A second test at a wash temperature of 49° C. gives similar results. At an equivalent weight level, the present builder outperforms sodium tripolyphosphate in calcium control. Products formulated as above give excellent hot or cold water cleaning ability.

EXAMPLE III

A product according to the present invention is prepared utilizing 20 parts builder prepared by Example I, 12 parts of the triethoxylated alcohol (dodecyl) and 50 parts water. The detergent product so formulated is fully miscible and shelf-stable, i.e. without separation of the components. The product, when tested, performs superior to a similarly formulated unbuilt detergent composition.

What is claimed is:

1. A compound of the formula:

[MOOCCH$_2$(MOOC)CHOCH$_2$]$_2$CHOCH-(COOM)CH$_2$COOM    (I)

wherein M is a salt-forming cation or hydrogen or mixtures thereof.

2. A compound of the formula:

HOCH$_2$CH[OCH(COOM)CH$_2$COOM]CH$_2$OH    (V)

wherein M is a salt-forming cation or hydrogen or mixtures thereof.

3. A detergent builder composition comprising a compound of the formula:

[MOOCCH$_2$(MOOC)CHOCH$_2$]$_2$CHOCH-(COOM)CH$_2$COOM    (I)

in admixture with one or more compounds of the formula:

HOCH$_2$CH(OH)CH$_2$OCH(COOM)CH$_2$COOM;    (II)

HOCH$_2$CH[OCH(COOM)CH$_2$COOM]CH$_2$OCH-(COOM)CH$_2$COOM;    (III)

MOOCCH$_2$(MOOC)CHOCH$_2$CH(OH)CH$_2$OCH-(COOM)CH$_2$COOM;    (IV)

or

HOCH$_2$CH[OCH(COOM)CH$_2$COOM]CH$_2$OH    (V)

wherein M is a salt-forming cation or hydrogen or mixtures thereof.

4. The composition of claim 3 wherein M is hydrogen.

5. The composition of claim 3 wherein M is sodium.

6. The composition of claim 3 wherein M is potassium.

7. The composition of claim 3 wherein M is lithium.

8. The composition of claim 3 wherein M is selected from the group consisting of ammonium and substituted ammonium compounds.

9. The composition of claim 3 wherein M is calcium or magnesium.

10. The composition of claim 9 wherein M is ammonium.

11. The composition of claim 3 additionally comprising a surfactant material selected from the group consisting of alkyl ether sulfates, alkyl benzene sulfonates, alkyl sulfates, olefin sulfonates, paraffin sulfonates, alkyl polyglycosides, and alkoxylated alcohols, and mixtures thereof.

12. The composition of claim 11 wherein the surfactant is an alkyl benzene sulfonate.

13. The composition of claim 11 wherein the surfactant is an alkyl ether sulfate.

14. The composition of claim 11 wherein the surfactant is an alkyl polyglycoside.

15. The composition of claim 11 wherein the surfactant is an ethoxylated alcohol.

16. The composition of claim 11 containing an additional detergent builder material selected from the group consisting of 2-oxa-1,3,4-butanetricarboxylic acid salts, 2-oxa-1,1,3-propanetricarboxylic acid salts, zeolites, citrate salts, carbonate salts, silicates, phosphate salts and salts of nitrilotriacetic acid.

17. The composition of claim 16 wherein the additional detergent builder material is sodium carbonate.

18. The composition of claim 16 wherein the additional detergent builder material is sodium tripolyphosphate.

19. The composition of claim 16 wherein the additional detergent builder material is the sodium salt of nitrilotriacetic acid.

20. The composition of claim 11 which further comprises water and thereby constitutes liquid detergent product.

21. A process for preparing a detergent builder composition comprising a compound of the formula:

[MOOCCH$_2$(MOOC)CHOCH$_2$]$_2$CHOCH(COOM)CH$_2$COOM        (I)

in admixture with one or more compounds of the formula:

HOCH$_2$CH(OH)CH$_2$OCH(COOM)CH$_2$COOM;        (II)

HOCH$_2$CH[OCH(COOM)CH$_2$COOM]CH$_2$OCH(COOM)CH$_2$COOM;        (III)

MOOCCH$_2$(MOOC)CHOCH$_2$CH(OH)CH$_2$OCH(COOM)CH$_2$COOM;        (IV)

or

HOCH$_2$CH[OCH(COOM)CH$_2$COOM]CH$_2$OH        (V)

wherein M is a salt-forming cation or hydrogen or mixtures thereof; said process being conducted by reacting glycerin with a source of maleic acid in the presence of an alkaline earth hydroxide at a temperature of from 50° C. to 125° C. and at a pH of greater than 10 and less than 14.

22. The process of claim 21 wherein the source of maleic acid is maleic anhydride.

23. The process of claim 21 wherein the reaction between the glycerin and the maleic acid source is conducted in the presence of both an alkaline earth hydroxide and an alkali metal hydroxide.

24. The process of claim 23 wherein the mole ratio of alkaline earth hydroxide to alkali metal hydroxide is from about 3:2 to about 1:6.

25. The process of claim 21 wherein maleic anhydride is employed as the maleic acid source and wherein the reaction is conducted without a preliminary step involving the hydrolysis of said maleic anhydride to maleic acid.

26. The process of claim 25 wherein an mixture comprising glycerin, the alkaline earth hydroxide and water is initially prepared and wherein substantially all of the maleic anhydride is subsequently added thereto in a single addition.

27. The process of claim 26 wherein the reaction is conducted in the presence of both an alkaline earth hydroxide and an alkali metal hydroxide.

28. The process of claim 27 wherein the mole ratio of alkaline earth hydroxide to the alkali metal hydroxide is from about 3:2 to about 1:6.

29. The process of claim 21 wherein maleic anhydride is employed as the source of maleic acid and is at least partially hydrolyzed to maleic acid prior to being employed in the reaction process and wherein a portion of the hydrolyzed maleic anhydride and a portion of the alkaline earth hydroxide are withheld from the reaction process during an initial reaction period and wherein said withheld portions are subsequently introduced into the reaction mixture in one or more incremental additions.

30. The detergent builder composition of claim 3 which comprises a compound of the Formula I in admixture with a compound of the Formula II.

31. The detergent builder composition of claim 3 which comprises a compound of the Formula I in admixture with a compound of the Formula III.

32. The detergent builder composition of claim 3 which comprises a compound of the Formula I in admixture with a compound of the Formula IV.

33. The detergent builder composition of claim 3 which comprises a compound of the Formula I in admixture with a compound of the Formula III and a compound of the Formula IV.

34. The detergent builder composition of claim 3 which comprises a compound of the Formula I in admixture with a compound of the Formula II and a compound of the Formula III and a compound of the Formula IV.

35. The detergent builder composition of claim 3 which comprises a compound of the Formula I in admixture with a compound of the Formula V.

36. The detergent builder composition of claim 31 wherein the weight ratio of the Formula I compound relative to the Formula III compound is from 8:1 to 1:8.

37. The detergent builder composition of claim 32 wherein the Formula I compound: Formula IV compound weight ratio is from 8:1 to 1:8.

* * * * *